US006707384B1

(12) United States Patent
Shuman et al.

(10) Patent No.: US 6,707,384 B1
(45) Date of Patent: Mar. 16, 2004

(54) SENSOR OUTPUT ANALOG PROCESSING—A MICROCONTROLLER-BASED INSECT MONITORING SYSTEM

(75) Inventors: Dennis Shuman, Gainesville, FL (US); R. David Crompton, Calgary (CA)

(73) Assignee: The United States of America as represented by the Department of Agriculture, Washington, DC (US)

( * ) Notice: Subject to any disclaimer, the term of this patent is extended or adjusted under 35 U.S.C. 154(b) by 0 days.

(21) Appl. No.: 09/846,277

(22) Filed: May 2, 2001

(51) Int. Cl.[7] .............................................. G08B 23/00

(52) U.S. Cl. .................... 340/573.2; 340/540; 340/566; 250/338.1; 250/336.1

(58) Field of Search .............................. 340/573.2, 540, 340/566; 250/338.1, 336.1, 341.1, 359.1

(56) References Cited

U.S. PATENT DOCUMENTS

| 4,410,967 | A | | 10/1983 | Hendricks ..................... 367/87 |
|---|---|---|---|---|
| 4,937,555 | A | * | 6/1990 | Litzkow et al. ............. 340/540 |
| 5,005,416 | A | | 4/1991 | Vick et al. ..................... 73/587 |
| 5,473,942 | A | * | 12/1995 | Vick et al. ................... 340/573 |
| 5,563,799 | A | * | 10/1996 | Brehmer et al. ............ 364/481 |
| 5,594,654 | A | * | 1/1997 | Shuman et al. ............. 340/573 |
| 5,646,404 | A | * | 7/1997 | Litzkow et al. .......... 250/338.1 |

OTHER PUBLICATIONS

Shuman, D., et al., "An Electronic Fall–Through Probe Insect Counter Computer System for Monitoring Infestation in Stored Product Facilities", *ASAE Meeting Presentation Paper No. 946501*, Atlanta, Georgia, pp. 1–12, Dec. 13–16, 1994.

Hook, B., et al., "Digital I/O with the PC", *Dr. Dobbs Journal*, pp. 64–70, Apr. 1994.

White, N.D.G., et al., "The Development and Use of Pitfall and Probe Traps for Capturing Insects in Stored Grain", *Journal of the Kansas Entomological Society*, vol. 63(4), pp. 506–525, Jul. 15, 1990.

Reed, C.R., et al., "Pitfall Traps and Grain Samples as Indicators of Insects in Farm–Stored Wheat", *Journal Econ. Entomol.*, vol. 84(4), pp. 1381–1387, Aug. 1991.

Hagstrum et al., *Proceedings 6th International Working Conference on Stored–Product Protection*, Canberra, Australia, 1994, in press.

Bauwin, G.R., et al., "Sampling, Inspection, and Grading of Grain", In: *Storage of Cereal Grains and Their Products; 2nd Ed.*, ed. C.M. Christensen, pp. 115–157, 1974; St. Paul, MN: American Association of Cereal Chemists.

Noyes, R., et al., "Stored Grain Management Techniques", In: *Management of Grain, Bulk Commodities, and Bagged Products*, Circular E–912, 71–79, Cooperative Extension Service, Oklahoma State University, 1991.

Hagstrum, D., et al., "How to Sample Grain for Insects", In: *Management of Grain, Bulk Commodities, and Bagged Products*, Circular E–912, 65–69, Cooperative Extension Service, Oklahoma State University, 1991.

(List continued on next page.)

*Primary Examiner*—Jeffery Hofsass
*Assistant Examiner*—Hung Nguyen
(74) *Attorney, Agent, or Firm*—John D. Fado; Gail E. Poulos

(57) ABSTRACT

A system for automated monitoring of pest insects in stored products to help identify insect species and improve reliability across adverse external conditions, including environmental, biological and aging. The system includes sensor units having a microcontroller which collects, analyzes, and stores data from a signal pulse created by an insect falling through the sensor unit.

14 Claims, 9 Drawing Sheets

Microfiche Appendix Included
(1 Microfiche, 56 Pages)

OTHER PUBLICATIONS

Hendricks, D.E., "Portable Electronic Detector System Used with Inverted–Cone Sex Pheromone Traps to Determine Periodicity and Moth Captures", *Environmental Entomology*, vol. 14(3), pp. 199–204, Jun. 1985.

Hendricks, D. E., "Development of an Electronic System for Detecting Heliothis spp. Moths (Lepidoptera: Noctuidae) and Transferring Incident Information from the Field to a Computer", *J. Econ. Entomol.*, vol. 82(2), pp. 675–684, Apr. 1989.

Shuman, D., "Infrared Bug–Counter Goes to Disney World", *Greenhouse Product News*, pp. 23–24, Jan. 1995.

Shuman, D., "Infrared Bug–Counter Goes to Disney World", *Agricultural Research Magazine*, p. 31, Oct. 1994.

Petitt, F.L., et al., "An Automated System for Counting and Packaging A Leafminer Parasitoid", *Florida Entomol. Soc.*, Aug. 1994. Poster presentation and press release by Sean Adams.

Subramanyam, BH., et al., "Accuracies and Sample Sizes Associated with Estimating Densities of Adult Beetles (Coleoptera) Caught in Probe Traps in Stored Barley", *J. Econ. Entomol.*, vol. 83(3), pp. 1102–1109, Jun. 1990.

Subramanyam, BH., et al., "Insects Infesting Barley Stored on Farms in Minnesota", *J. Econ. Entomol.*, vol. 82(6), pp. 1817–1824, Dec. 1989.

Barak, A.V., et al., "Factors Affecting the Design of Traps for Stored–Product Insects", *Journal of the Kansas Entomological Society*, vol. 63(4), pp. 466–485, 1990.

Cuperus, G.W., et al., "Variables Affecting Capture of Stored–Grain Insects in Probe Traps", *Journal of the Kansas Entomological Society*, vol. 63(4), pp. 486–489, 1990.

Wei, Y., et al., "Computerized Remote Control System for Monitoring Dynamics of Insect Population in Bulk Stored Grain", *6th International Working Conference on Stored Product Protection*, Canberra, Australia, Apr. 1994.

Shuman, D., et al., "Automated Monitoring of Stored–Grain Insects: Acoustical and Electronic Probe Methods", Presentation: *Annual International Research Conference on Methyl Bromide Alternatives and Emissions Reductions*, Nov. 1994.

Shuman, D., "Electronic Detection of Insects in Grains", Hand–out at ARS/FGIS Working, with Non–Gov't People Present, Oct. 25, 1991.

Subramanyam, BH., et al., "Field Tests with Probe Traps for Sampling Adult Insects Infesting Farm–Stored Grain", *J. Agric. Entomol.*, vol. 6(1), pp. 9–21, Jan. 1989.

Trece Incorporated, *Storgard WB Probe II Insect Monitoring System*, 1 page.

AgriSense BCS Ltd., Trappit Insect Probe Trap (Technical Information), 1 page.

* cited by examiner

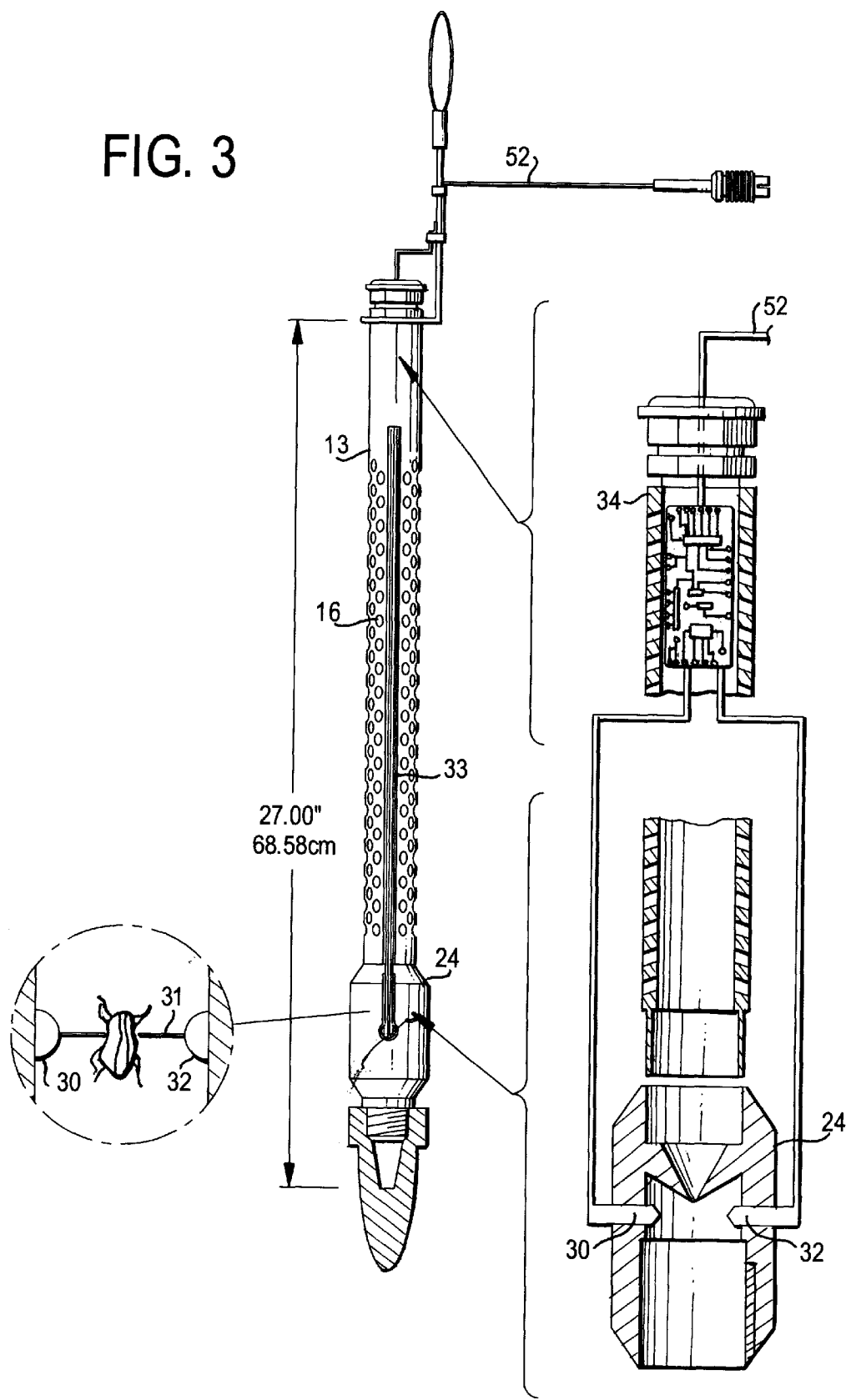

SENSOR OUTPUT ANALOG PROCESSING—A MICROCONTROLLER-BASED INSECT MONITORING SYSTEM

MICROFICHE APPENDIX

A Microfiche Appendix containing 1 microfiche containing 56 frames is included.

BACKGROUND OF THE INVENTION

1. Field of the Invention

This invention generally relates to an apparatus and a process for monitoring and/or providing a quantitative and/or qualitative indication of insect infestations in stored products.

2. Description of the Related Art

Protection of stored agricultural commodities from insect infestations and the direct loss caused by insects are costly. Insect infestations in stored agricultural commodities result in annual losses of millions of dollars. Early detection of infestation problems is necessary to initiate timely control measures and eliminate unnecessary "scheduled" insect treatments. Routine use of insecticides to protect stored products may have constraints.

The standard practice for detecting and quantifying infestation in stored grain is visual inspection of samples for adult insects. Insects are usually separated from grain samples with hand or inclined sieves. A traditional method of obtaining samples uses a long, hollow multi-compartment grain trier inserted into the commodity. Its gates are then opened and closed to acquire samples at different depths and, after withdrawal, the samples are removed for inspection (Bauwin et al., In: Storage of Cereal Grains and Their Products; $2^{nd}$ edition, ED: C. M. Christensen, 115–157, 1974; St. Paul, Minn. :American Association of Cereal Chemists). Other methods can get beyond the limitation of only sampling close to the grain's surface. A vacuum probe can extract larger samples from deeper with a grain mass and a grain mass can be turned enabling a pelican sampler to catch samples from the moving grain stream (Noyes et al., In: Management of Grain, Bulk Commodities, and Bagged Products, Circular E-912, 71–79, Cooperative Extension Service, Oklahoma State University, 1991). None of these sampling techniques provide continuous and thorough monitoring. Low insect populations are difficult to detect in small samples and a much greater proportion of the grain needs to be sampled to accurately estimate insect population size (Hagstrum et al., IN: Management of Grain, Bulk Commodities, and Bagged Products, Circular E-912, 65–69, Cooperative Extension Service, Oklahoma State University, 1991). Additionally, theses sampling methods are expensive and labor intensive and therefore not repeated very often even though an infestation can grow from undetectable to damaging levels in two weeks. Another method, employed in some large grain elevators, is temperature sensing cables distributed throughout the storage volume. This system is only sensitive to very high insect populations. Furthermore, both moisture and mold growth can elevate temperature levels.

White et al., (Journal of the Kansas Entomological Society, Volume 63(4), 506–525,1990) and Reed et al. (Journal of Economic Entomology, Volume 84(4), 1381–1387, 1991) both disclose passive grain probe traps that have been developed. The probes are vertical perforated tubes that insects crawl into and then drop through to be trapped in a reservoir at the lower end. Probes are left in the grain for prolonged periods, allowing them to continuously capture insects and thus detect very low insect populations. However, the information is only available after the labor intensive process of inserting the trap into the grain, waiting, withdrawing the trap, and then inspecting the trap contents. The difficulty of insertion and withdrawal increases with the distance from the surface due to the resistance of the grain.

U.S. Pat. No. 5,005,416 discloses an automated, continuous monitoring electronic grain probe trap with a bottom reservoir fitted with a detector that senses the movements of trapped insects. The number of insects caught in the trap is estimated based on the amount of vibration detected. However, temperature, species, time in the trap, the amount of food, and other insects in the trap are all factors which can affect the trapped insects' vibration producing activity. Vibration detection may also be prone to error from ambient noise.

Hagstrum et al. (Proceedings $6^{th}$ International Working Conference on Stored-Product Protection, Canberra, Australia, Volume 1, 403–405, 1994) disclose a computer-based acoustic system that provides for automated monitoring by detecting insect generated sounds. Piezoelectric transducers, mounted on vertical cables installed in grain bins, sense the feeding and movement sounds of nearby insects. The acoustic sensor outputs are sequentially connected to electronic components that count and relay to a computer, the number of signal peaks crossing a threshold level during each sensor's observation interval.

U.S. Pat. No. 5,646,404 (herein incorporated by reference) discloses an electronic grain probe insect counter (EGPIC) which provides real-time monitoring of insects using infrared beam technology to detect insects as they fall through modified grain probe traps. When an insect falls through the trap, it partially masks an infrared beam. Whenever one of the traps infrared-beam sensor output signals exceeds a precise detector threshold level (this level being set to specify the minimum detectable insect size), the resulting quantitative insect detection or count is recorded and time-stamped to provide an ongoing indication of infestation levels in stored-products. The real-time data acquired by an EGPIC system are used to display the numbers of insects that have been counted within specific commodity regions and time periods. If the rate of insect counts are below a known threshold (based on factors such as economics, tolerance, environmental parameters, etc.), no control action is necessary. However, if the rate is above that threshold, the appropriate response may be a function of the species being counted. This is because the relationship between insect counts and population density is a function of species. Therefore, the appropriate first response may be to go into the commodity storage and identify the species at those probe sites that are getting the high insect counts. Then, with that species information, a decision can be made as to if and what control response is warranted. Thus, while the EGPIC system can eliminate the need to visually inspect the commodity on an ongoing scheduled basis, increasing insect counts may still mandate a visual inspection before control decisions are made. The EGPIC system employs a sensitivity control in order that it not count objects smaller than the smallest stored-product insect of concern (e.g., grain particles). Because of this, smaller insects such as psocids and mites are not counted even though their presence may be of interest to the facility manager. This sensitivity control must be set conservatively (higher sensitivity) in order to ensure that each probe maintains a reasonable count accuracy with the smallest stored-product insect of concern because of large electronic and mechanical component variability across probes. However, this may occasionally lead to false positives due to other very small insects (e.g., psocids) and grain particles. Other potential sources of false positives are electrical impulse noise (e.g., generated by electric machinery) and a crawling or clinging insect managing to get near the infrared beam which can cause a multitude of false counts. The EGPIC system has a self-test feature to insure that receiving no counts from a probe is not an indication of a probe or system failure. At regular time intervals, the system momentarily decreases the infrared beam source output, simulating an insect falling through and masking part of the beam, and then checks whether this "count" is detected. However, this is a pass/fail test, so there is no warning of a gradual performance degradation until failure occurs.

While various methods and systems have been developed for monitoring insect infestations in stored-products, there remains a need in the art for a system for remote monitoring of pest infestations which provides a more accurate count and species identification. The present invention provides a remote system for automatically counting insects which enables a qualitative analysis of an analog sensor output signal to provide additional information that can help identify species, reject erroneous counts, etc. which is different from prior art methods and systems.

SUMMARY OF THE INVENTION

It is therefore an object of the present invention to provide a monitoring system for insect infestations in stored-products that gives both accurate counts and qualitative information such as insect species identification.

Another object of the present invention is to provide a monitoring system that counts all objects falling past a sensing transducer including those that are not identified as insect species of concern and the ability to discriminate between the different falling object categories.

A further object of the present invention is to provide a monitoring system that has a means for obtaining identical response sensitivity from all probes despite large electronic and mechanical component variability across probes.

A still further object of the present invention is to provide a monitoring system which obtains consistent response sensitivity from each probe despite changes resulting from component aging, environmental changes, and potential foreign matter accumulation (e.g., dust, moisture, etc.) on the system's sensing transducer components.

Another object of the present invention is to provide a monitoring system which monitors the ongoing performance of each deployed probe while in situ, thus obtaining an indication of a forthcoming need for probe maintenance before probe failure.

A still further object of the present invention is to provide a monitoring system which improves system accuracy by only counting insects falling past the system's sensing transducer while rejecting potential detection of insects inadvertently loitering in the vicinity of the sensing transducer.

Another object of the present invention is to provide a monitoring system which improves system accuracy by rejecting false detections due to electrical transients (noise spikes).

Further objects and advantages of the invention will become apparent from the following description.

BRIEF DESCRIPTION OF THE DRAWINGS

FIG. 3 is a drawing of a probe showing the location of temperature sensor 33, probe circuit board 34, and sensor head 24.

DETAILED DESCRIPTION OF THE INVENTION

Figure 1:
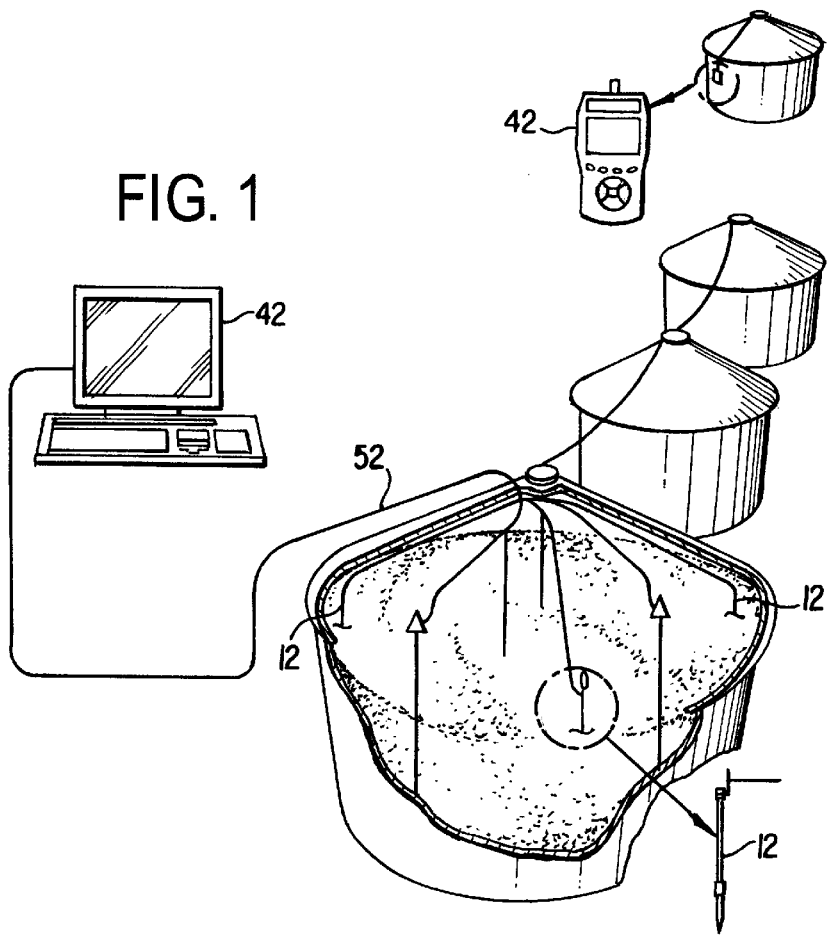
FIG. 1 is a drawing showing placement pattern of a microcontroller-based insect monitoring system in a grain storage facility.
Figure 2:
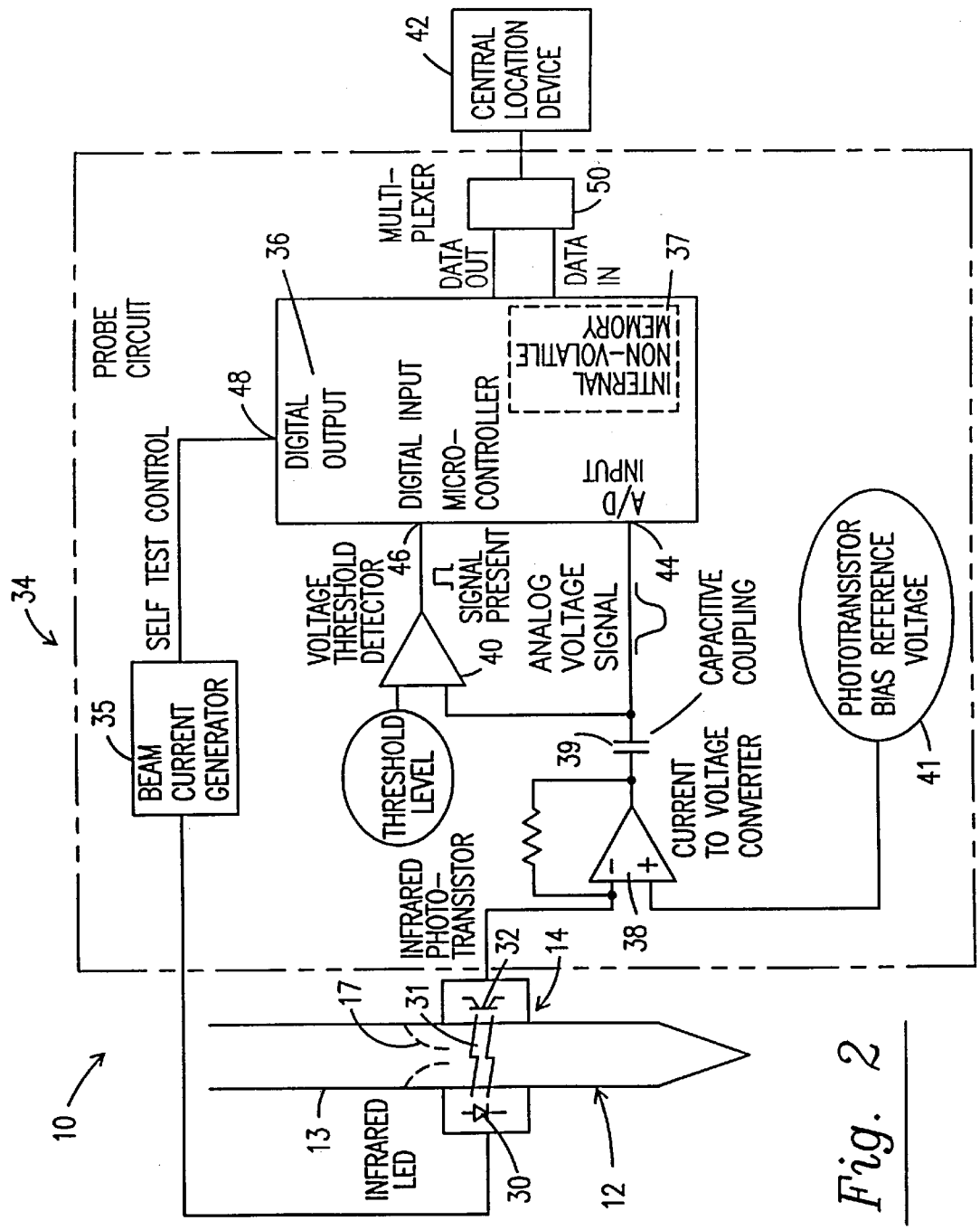
FIG. 2 is a block diagram showing a microcontroller-based insect monitoring system implemented with infrared tranducers.

The present invention is useful for providing a quantitative and/or qualitative detection of insect infestations in stored products such as grains, fruits, nuts, vegetables, and legumes, for example (FIGS. 1 and 2). Enhancement of a grain probe trap with a microcontroller-based insect monitoring system 10, eliminates (a) the labor intensive process involved in its use, (b) the limitations on where it can be located in a storage structure, and (c) the lack of information available from it until removed for the stored commodity and inspected.

The present invention not only determines when an analog output signal of a sensing transducer exceeds a certain threshold value to generate a digital pulse (FIG. 4) which is then counted; it also acquires and analyzes the sensor output signal waveform to extract additional information from it which is then utilized to determine, for example, (a) what insect species of concern are present, (b) if other objects are entering the probe, (c) the current probe sensitivity; (d) the need for forthcoming maintenance, and (e) to reject false positives due to either crawling insects or electrical noise spikes. It includes a sensing transducer with an analog output signal which can be, for example, an infrared beam receiver 32 (e.g., a phototransistor), a moisture sensor (e.g., a parallel plate capacitor), etc., and the information extracted from the output waveform of the transducer is primarily its amplitude and its duration. It can also include a smart sensor with built-in analog to digital conversion and signal processing, in which case the invention could be implemented, in whole or in part, in the sensor body itself.

For purposes of illustration, the following detailed description exemplifies the implementation of the present invention using an electronic grain probe insect detector having infrared beam transducers in the sensor head, such as for example, as described in U.S. Pat. No. 5,646,404 (Litzkow et al, Jul. 8, 1997; herein incorporated by reference); and Shuman et al. (A Computer-Based Insect Monitoring System for Stored-Products Using Infrared Sensors, presented at Third International Symposium on Sensors; in Horticulture, Aug. 17–21, 1997 in Tiberias, Israel; Proceedings in Acta Horticulturae, In press; herein incorporated by reference). One of ordinary skill in the art could readily incorporate any type of sensor capable of an analog output in which the waveform amplitude is indicative of insect species, given the detailed description provided below.

At least one transducer is mounted in sensor head 24 at the bottom of the upper probe body section 13. Each transducer is operatively connected to probe circuit board 34 through a transducer cable 25 (FIG. 3). Probe circuit board 34 is mounted near the transducer(s) within a distance that results in an acceptable degradation of transducer signals and susceptibility to electrically induced noise. One of ordinary skill in the art could readily determine the maximum distance for acceptable degradation of transducer signals and susceptibility to electrically induced noise.

Circuit board 34 (FIGS. 2 and 3) includes at least a programmable microcontroller 36 and a voltage threshold detector 40. Microcontroller 36 includes at least an analog input 44, a digital input 46, a digital output 48, and an internal non-volatile memory 37 containing a software program for analyzing a signal, measuring the duration of a signal, monitoring the signal for a maximum analog value, determining the realtime at object detection, and recording and storing the maximum analog value and its corresponding time-stamp for transmission to a central location device 42. For purposes of the present invention, the non-volatile memory is a computer readable medium. The computer readable medium must be capable of operatively interacting with a central location device 42. Each probe 12, having dedicated circuit board 34, processes the transducer output signal, stores the extracted data, and on command, transmits this data back through a transmission medium 52 to a central location device 42 (FIG. 2). A transmission medium is any medium through which data can be transmitted such as for example cables, including fiber optic cables; wireless, including radio links; etc. When probe 12 contains a temperature sensor 33 (FIGS. 2 and 3), a temperature reading is stored in memory 37 of microcontroller 36 each time an insect is detected as well as on scheduled intervals. This data is also transmitted with probe 12 extracted data in order to aid in the data interpretation. For the purposes of this invention, the central location device 42, by way of definition, is anything which can acquire, store, and display data, such as for example a computer, a hand-held monitor, etc. The data can be displayed as text or graphically to enhance the observation of trends. The central location device 42 can also analyze the data, for example, to determine the species of detected insects as described below in the detailed description of the invention. Other analyses can include, for example, spatial analysis to generate three dimensional insect population contours, expert systems to make insect management control decisions, etc.

In operation of the circuit board 34, the conditioned sensor output is connected to the following stages via a capacitive coupling 39 in order to present a signal to them only when a transducer output transient occurs as when an object passes near the transducer. This effectively eliminates the effects of slow changing transducer output signals due to such variables as changing environmental conditions or sensor component drift. Microcontroller 36 has an analog input 44 (analog to digital converter; A/D input) and non-volatile memory 37 as well as digital inputs 46 and outputs 58. The capacitively coupled sensor analog voltage signal is applied to analog input 44 (FIG. 6, Pin 2 of PIC16F872) as well as to a voltage threshold detector 40. The threshold level of detector 40 is set slightly above the electronic noise floor of the conditioned sensor voltage signal so that it generates a signal present digital pulse (FIG. 4) whenever any object passing near the transducer alters the transducers' output level. This signal present digital pulse, which persists as long as the sensor signal is greater than the threshold level, is connected to digital input 46 (FIG. 2) of microcontroller 36 to alert it to begin processing the signal coming in on its analog input 44. Microcontroller 36 stores the data extracted from sensor signals in its memory 37 and, upon request from a central location device 42, transmits this data back to it (FIG. 2).

Figure 5A:
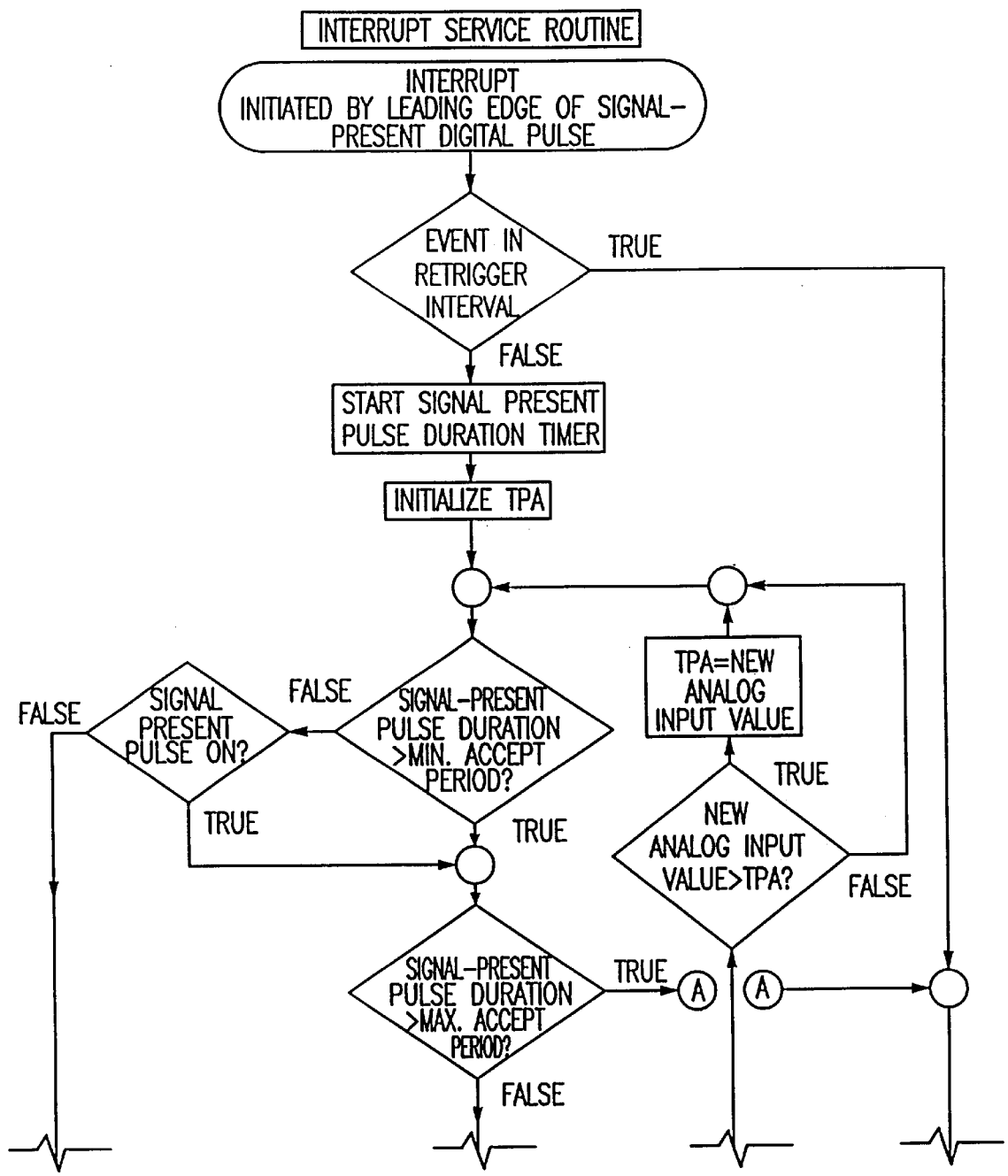
FIG. 5 is a flowchart of the signal processing program sub-component.
Figure 5B:
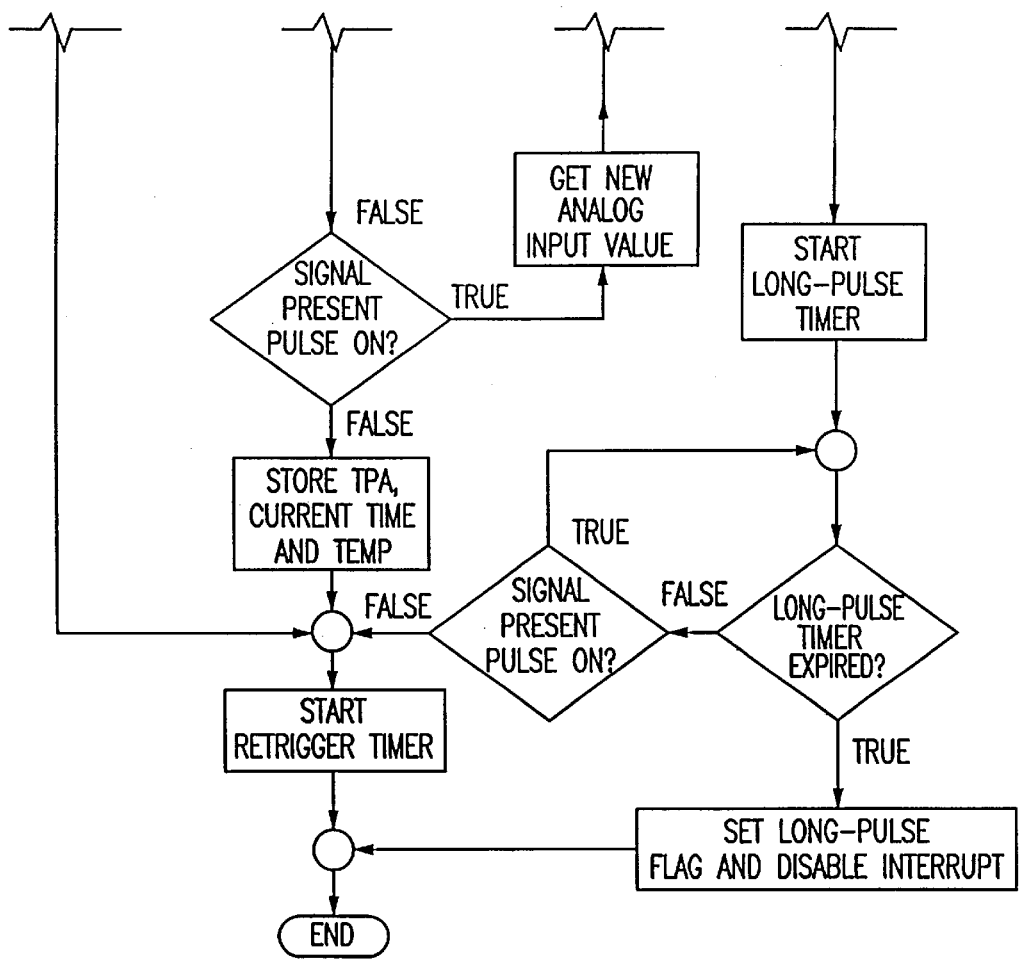
Figure 5C:
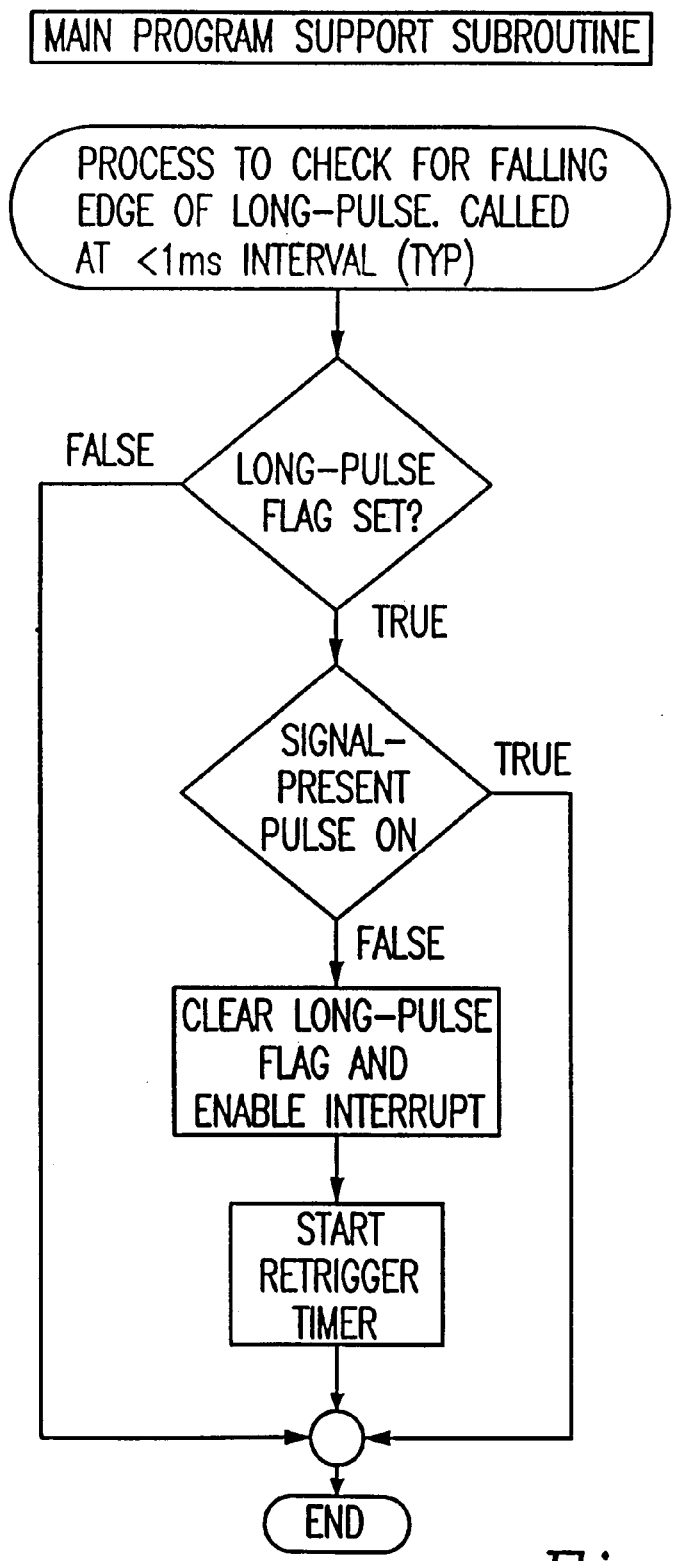

The sensor output analog processing microcontroller software program is written into the probe circuit at the time of manufacture of each probe after it is completely assembled. The software program includes a signal processing sub-component, a calibration sub-component, and a data transmission sub-component embedded in a main program loop. The signal processing sub-component operation is summarized in a software flowchart (FIG. 5). It contains an interrupt service routine that is called by the main program to analyze the incoming sensor signal whenever the leading edge of an incoming signal present digital pulse generates an interrupt via the digital input 46 (FIG. 2). A signal present digital pulse usually indicates that an insect is falling past a transducer. The falling insect simultaneously results in a sensor analog voltage signal applied to the analog input 44 of microcontroller 36, whose instantaneous amplitude is determined by some physical property of the insect indicative of its species as sensed by the transducer. The interrupt service routine monitors the analog sensor signal during the presence of the signal present digital pulse, and stores the maximum analog value attained during the signal present digital pulse interval and its time of occurrence (timestamp). This stored value is called the Target Peak Amplitude (TPA) of the analog signal, and it is achieved during the excursion of the insect past the transducer. It is statistically proportional to some physical property of the insect. However, there can be a significant variability in the distribution of these Target Peak Amplitudes obtained when multiple insects of the same species fall past the transducer. Since these distributions for different insect species may overlap, it may not be possible to positively identify the species of each falling insect by the Target Peak Amplitude of its generated analog signal. Even so, when a number of insects of the same species falls past the transducer, a distribution pattern emerges with a mean and variance that can be used to identify that species. In those situations where the identity of the species cannot be ascertained with absolute certainty, it can be narrowed down to those with similar physical properties, and then may be narrowed down even further by knowing the predominant species in a particular geographic region. The validity of this statistical approach is based on empirical evidence that stored-product insects of any one species tend to aggregate in clusters so that the vast majority of insects entering a particular probe during a limited time interval will be of the same species.

Since the signal present digital pulse is generated whenever any object passes near the transducer, objects other than stored-product insects of concern will also get recorded. However, since their Target Peak Amplitudes are recorded, these detections will not erroneously be counted as stored-product weevils or beetles. In fact, these other counts may provide useful information about the presence of other targets such as, for example, mites, psocids, predator insects, grain particles, etc.

Another function of the interrupt service routine is to monitor the duration of the signal present digital pulse. Since the range of time it takes for an object to fall past a transducer is known, the microcontroller is programmed to not record events when the signal present digital pulse durations are not within some known range in order to prevent false positives (erroneous counts) Electrical transients or noise spikes, that may be generated by electric machinery or electronic current surges, are typically a few microseconds in duration and almost always less than about 1 msec. Therefore, they would not be recorded despite the fact that their Target Peak Amplitudes may be comparable to those produced by falling insects. Also, in the unlikely event that an insect is able to loiter in the vicinity of the transducer or by crawling onto the surface of the transducer(s), a series of false signal present digital pulses may be generated. However, these are almost always greater than some known time duration and would therefore not be recorded. To provide additional protection against false positives due to loitering insects, microcontroller 36 is programmed to not record any signal present digital pulse generated within a specified retrigger interval (described below) of the end of a previously generated signal present digital pulse, even if the previous signal present digital pulse's duration was not within the acceptable range and therefore not recorded. This retrigger interval also prevents multiple counts from being recorded when a single insect falls past the transducer, either due to an irregular (double peaked) shaped analog waveform or due to grain particles being pulled in by the insect when it enters a probe.

The above features are accomplished by the signal processing sub-component as shown in the software flowchart (FIG. 5). When the leading edge of an incoming signal present digital pulse generates an interrupt, the interrupt service routine first checks whether the interrupt is within the retrigger interval from the end of the preceding signal present digital pulse. In the non-retrigger case where a signal present digital pulse begins sufficiently after any previous falling insect, the interrupt service routine moves down the central column shown in the flowchart (FIG. 5). First the interrupt service routine starts a signal present digital pulse duration timer and sets an initial Target Peak Amplitude value. It then enters an analysis loop where it begins by checking the signal present digital pulse duration timer. If the elapsed time is less than a known minimum acceptable period (sensor specific) and the signal present digital pulse is no longer present (indicative of a noise spike), then the interrupt service routine drops out of the analysis loop, the retrigger interval timer is started, and the interrupt service routine ends. If not, the interrupt service routine continues down the central column and again checks the signal present digital pulse duration timer. If the elapsed time is greater than a known maximum acceptable period (indicative of a crawling insect), then the interrupt service routine drops out of the analysis loop and a long-pulse timer (discussed below) is started. If not, the interrupt service routine continues down the central column and checks for the presence of the signal present digital pulse. If the signal present digital pulse is still present, then the interrupt service routine reads the current value of sensor analog voltage signal and compares it with the stored Target Peak Amplitude value. If the current value is larger, then it becomes the new Target Peak Amplitude value, or else the previous Target Peak Amplitude value remains. In either event, the interrupt service routine returns back to the beginning of the analysis loop where it previously checked the signal present digital pulse duration timer for some minimum acceptable period elapsed and the process repeats itself. If the signal present digital pulse ends while the interrupt service routine is going around the analysis loop (indicative of an insect falling past the transducer within the acceptable time range), it drops out in the central column to store the Target Peak Amplitude, current time, and temperature. Then the retrigger interval timer is started and the interrupt service routine ends.

In the retrigger case of an object falling past a transducer in less time than the retrigger interval after a previously falling object, indicating that the incoming analog waveform should be ignored, the central column of the signal processing routine is bypassed and the long-pulse timer is begun. The function of this timer is to prevent an extremely long signal present digital pulse (e.g., due to a crawling insect) from tying up microcontroller 36 and preventing it from accomplishing its other tasks such as staying in communication with the central location device. If the signal present digital pulse lasts less than the time-out duration of the long-pulse timer, then the retrigger interval timer is started and the interrupt service routine ends, or else a long pulse flag is set which disables further interrupts, and then the interrupt service routine ends. The long-pulse timer insures that the maximum duration of the interrupt service routine (which occurs in the non-retrigger case when the maximum acceptable period in the analysis loop is followed by a time-out of the long-pulse timer) is limited. A support subroutine (shown in the flowchart), which is regularly called by the main program while performing its other tasks, checks for the continued presence of an ongoing signal present digital pulse (i.e., a signal present digital pulse that continues beyond the end of the interrupt service routine it initiated) whenever the long pulse flag is set. Once an ongoing signal present digital pulse ends, the support subroutine clears the long-pulse flag (which re-enables interrupts), starts the retrigger interval timer, and microcontroller 36 is again ready to receive input signals from the transducer(s).

The function of the calibration sub-component of the microcontroller program is to help provide consistent performance across probes despite large component tolerances and varying environmental conditions over longtime usage. Consistent qualitative performance is of importance since the values of the Target Peak Amplitudes will be utilized to make management decisions instead of just the quantitative insect count response. The calibration sub-component consists of two different response sensitivity initialization routines and then ongoing self-tests. Newly manufactured probes have an initial range of response sensitivity due to component tolerances, especially transducer electrical parameters and sensor head mechanical tolerances. The first initialization procedure, performed with each new probe, consists of dropping a number of small known basic objects through the exact center of the sensor head. The Mean of the Basic target Peak Amplitudes (MBPA) from these drops is permanently recorded in the non-volatile memory of the microcontroller chip as a calibration factor. When a probe is put into service and it transmits its collected Target Peak Amplitude data back to a central location device for storage and display, this Mean of the Basic target Peak Amplitudes number is also transmitted. There it is used to adjust the incoming Target Peak Amplitude data before they are stored and displayed. This normalization is accomplished by dividing the incoming Target Peak Amplitudes by the Mean of the Basic target Peak Amplitudes, thus making all new probes appear to have identical sensitivity response performance. Although this mathematical operation could be accomplished by the microcontroller prior to transmission of Target Peak Amplitude data, it is left to the central location device in order to reduce the overhead (computational load) of the microcontroller. The second initialization procedure involves the system self-test feature. The microcontroller can generate a digital test pulse that results in a momentarily change in the transducer output which simulates the passing of an insect near the transducer. By performing this self-test at regular intervals, the system can validate proper operation of each probe. The second initialization procedure performs a self-test on each newly manufactured probe and the resulting peak amplitude (Initial Self-test Peak Amplitude, ISPA) is permanently recorded in the microcontroller's non-volatile memory. When a probe is put into service, this Initial Self-test Peak Amplitude number is also transmitted to the central location device. While the probe is in service, its self-test is performed at regular intervals, for example, about every hour. The resulting peak amplitude, called the Current Self-test Peak Amplitude (CSPA) is also transmitted to the central location device. This Current Self-test Peak Amplitude may differ from the Initial Self-test Peak Amplitude due to changes such as component aging, environmental changes, and potential foreign matter accumulation such as dust, moisture, etc., on the transducer components. In order to reduce the effect of such changes in the interpretation of the peak amplitude data, the ratio of the Initial Self-test Peak Amplitude to the Current Self-test Peak Amplitude is used as a factor to adjust the target data. Therefore, utilizing all the above calibration data, the Adjusted Target Peak Amplitude (ATPA) can be expressed as:

$$ATPA=(TPA/MBPA)\times(ISPA/CSPA)$$

This adjustment tends to make all probes appear to have identical sensitivity response performance even while they are in service for long periods under varying environmental conditions. As before, although this calculation could be accomplished by the microcontroller, it is left to the central location device in order to reduce the overhead of the microcontroller. If the actual sensitivity response degrades too much resulting in very low Target Peak Amplitudes, the probe may become unreliable or nonfunctional and require maintenance such as cleaning and/or repair. However, by continuously monitoring changes in the Current Self-test Peak Amplitude, any gradual degradation in the sensitivity response will be observed. This will allow maintenance to be scheduled and performed before catastrophic failure occurs.

The data transmission sub-component of the microcontroller program performs the task of transmitting the stored Target Peak Amplitudes and the calibration factors back to the central location device upon its request. As previously stored Target Peak Amplitude data are transmitted back, the microcontroller memory is cleared for storing newly acquired Target Peak Amplitude data.

The following example is intended only to further illustrate the invention and is not intended to limit the scope of the invention which is defined by the claims. Infrared transducers are used as a model to exemplify the system of the present invention.

EXAMPLE

The operation of system 10 is described using an infrared phototransistor 32 and an infrared light-emitting diode 30 as transducers (FIGS. 2 and 3). Phototransistor 32 is operated with reversed collector and emitter connections to reduce its gain, and thus, keep the phototransistor 32 in it's linear region so that it's output signal is proportional to the amount of light masked by the insect passing through beam 31.

The probe body used for this example was made of PVC pipe and contained 210 apertures 16 arranged in 10 rows with 21 apertures 16 per row. Sensor head 24 was fabricated out of extruded black nylon 6/6 to reduce internal infrared light reflections. Its inner surface was also sandblasted to further reduce its reflectivity The probe body also included temperature sensor 33.

Circuit board 34 was mounted in the top of upper probe body section 13 less than about two feet from the infrared transducers. It included a programmable microcontroller 36, beam current generator 35, voltage threshold detector 40, current-to-voltage convertor 38, and multiplexer 50. The microcontroller is as described above in the detailed description. Each probe 12, having dedicated circuit board 34, processes the infrared phototransistor 32 output signal, stores the extracted data, and on command, transmits this data back through transmission cable 52 to a monitor or computer. The temperature is read by sensor 33 and is stored in memory 37 of microcontroller 36 each time an insect is detected. This data is also transmitted with the extracted data in order to aid in data interpretation.

Figure 4:
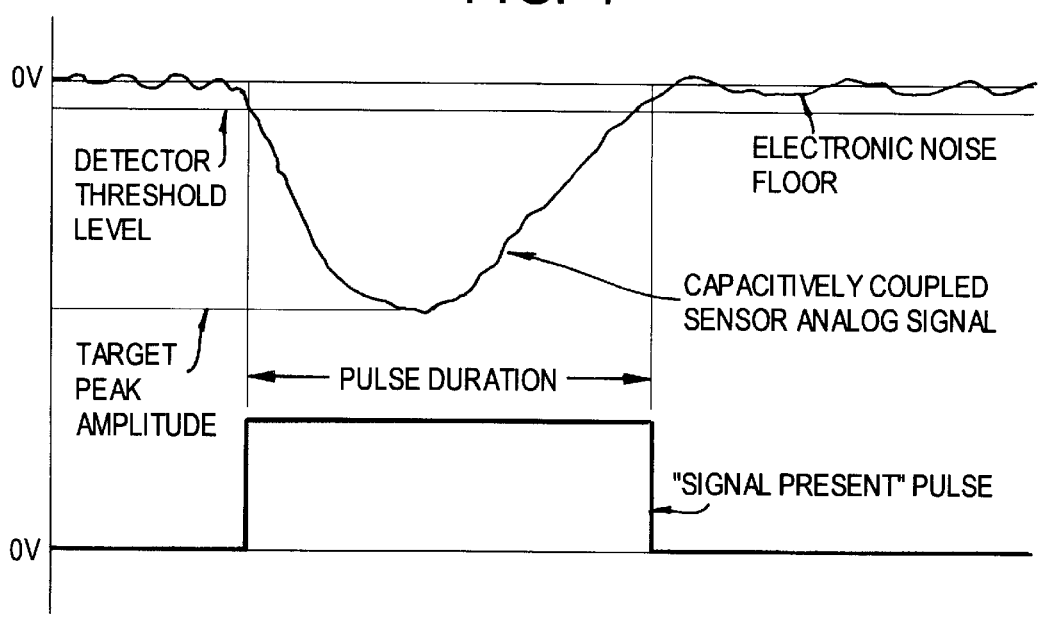
FIG. 4 is a graph showing the waveforms from the sensor output analog processing implementation.

The phototransistor 32 output current is conditioned by an operational amplifier configured as a current-to-voltage converter 38. This conditioning circuit implementation allows the phototransistor 32 bias voltage to be set by the bias reference voltage 41 applied to the operational amplifier. In this configuration, the bias voltage is. automatically maintained at the desired value independent of the phototransistor characteristics and therefore does not need to be regularly readjusted. The current-to-voltage convertor 38 output is then capacitively coupled in order to present a signal to the following stages only when a phototransistor 32 output transient occurs as when an insect passes through the infrared beam 31. This effectively eliminates the effects of slow changing phototransistor output signals due to such variables as changing environmental conditions or sensor component drift. For the infrared transducers, whenever any size object passes through the infrared beam, it generates a signal present digital pulse (FIG. 4). This pulse is connected to digital input 46 of microcontroller 36 (FIG. 6, Pin 21 of PIC 16F872) to alert it to begin processing the signal coming in on its analog input 44. Microcontroller 36 stores the data extracted from the sensor signals in memory 37 and, upon request from a central location device 42, transmits this data back to it, via Pin 23 of PIC 16F872 (FIG. 6), using a serial transmission protocol. Multiplexer 50 allows the single transmission channel 52 to be bidirectional, carrying both the data request and the stored data between microcontroller 36. and central location device 42.

Figure 6A:
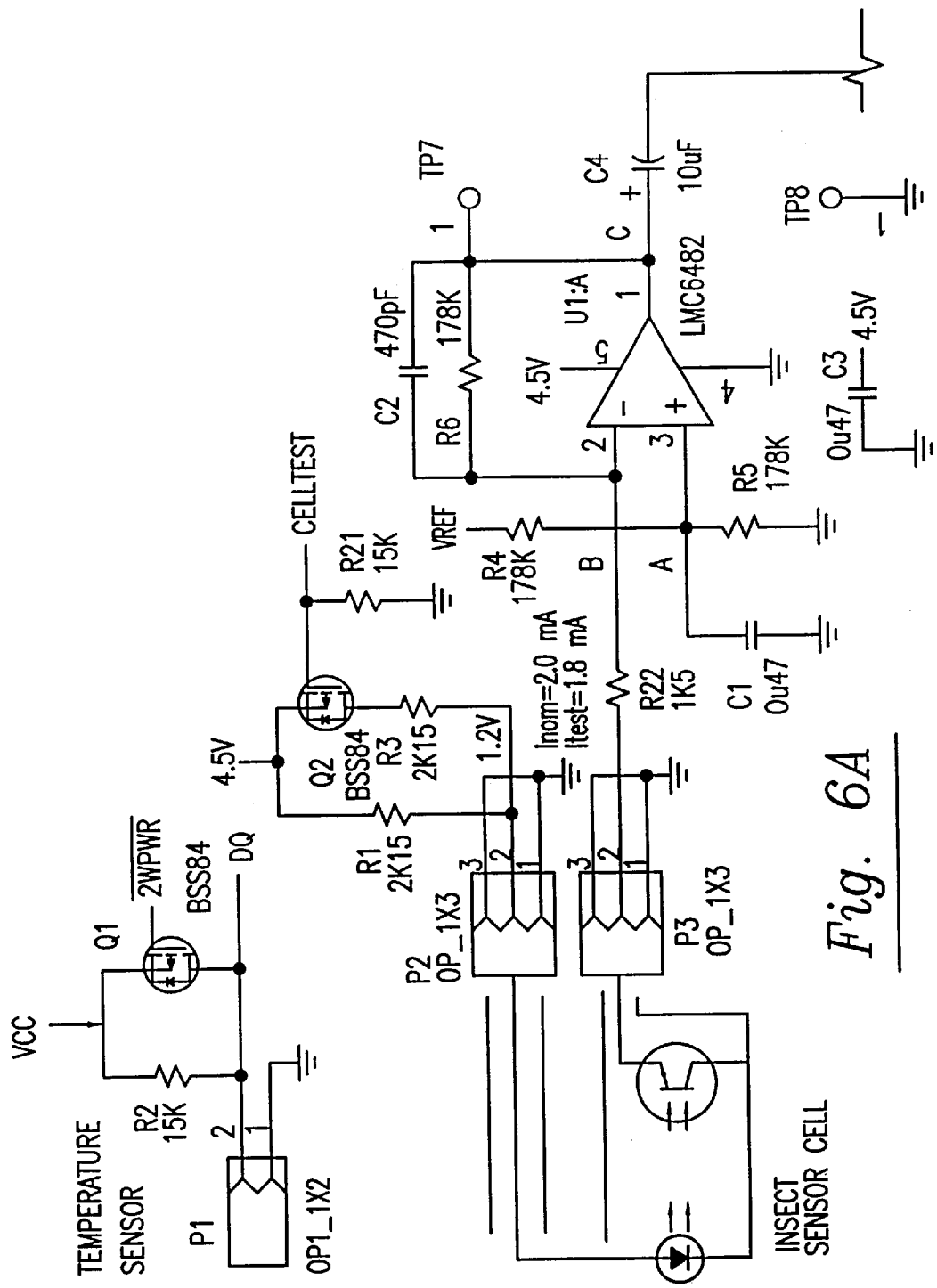
FIG. 6 is a detailed schematic of the probe circuit implemented with infrared transducers.
Figure 6B:
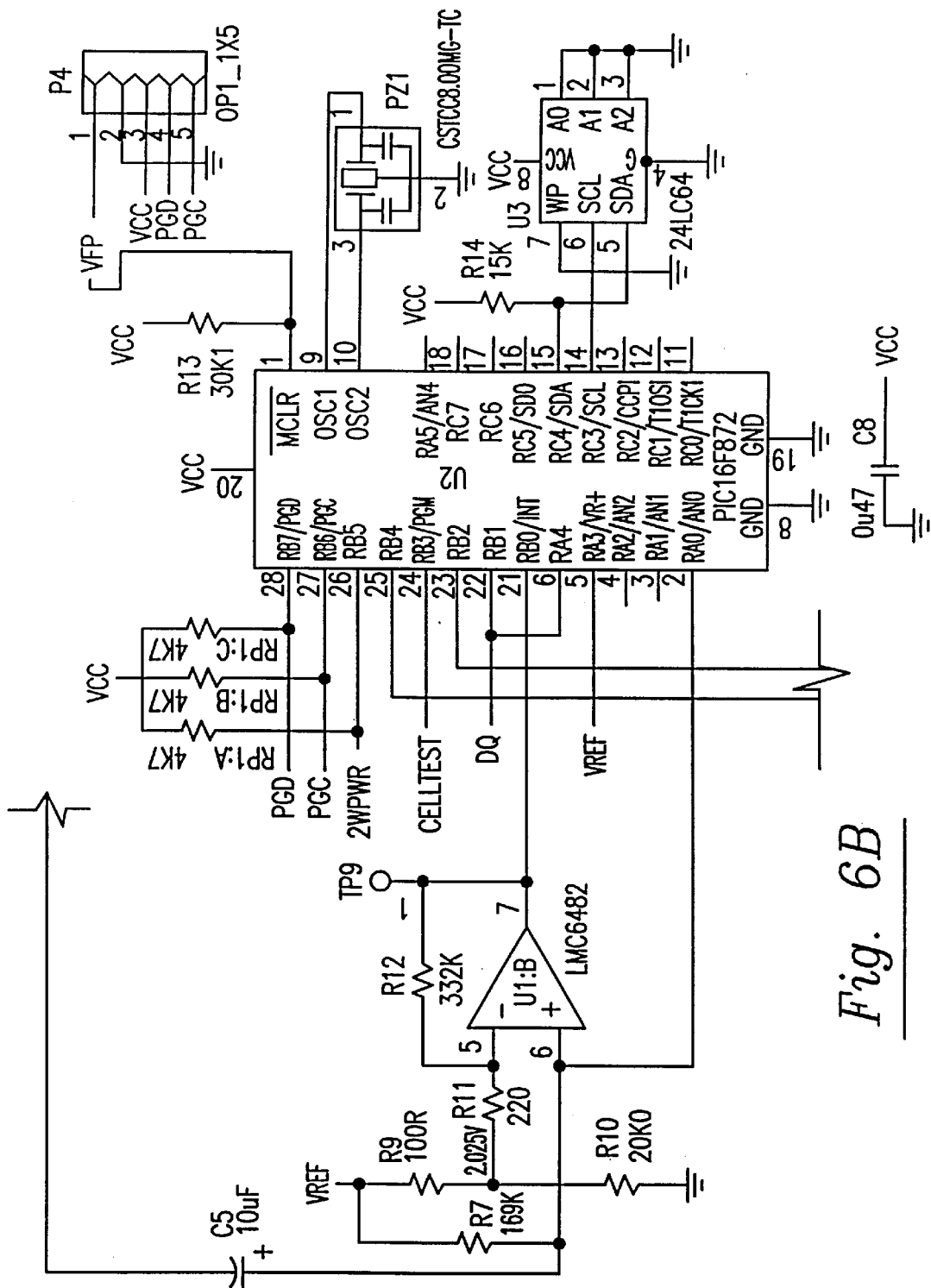
Figure 6C:
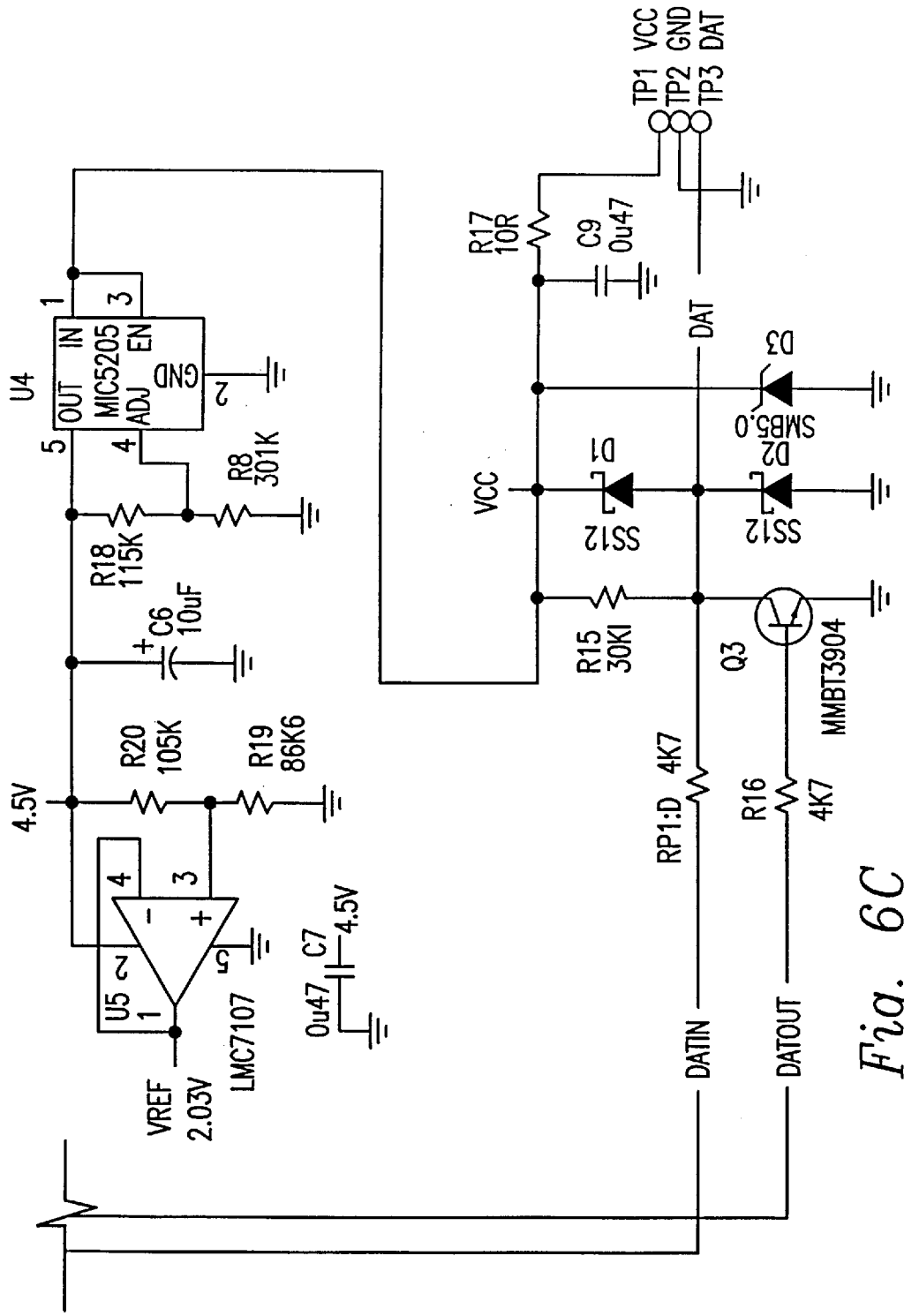

For the software program, the signal processing sub-component operation contains an interrupt service routine as described above in the detailed description. It is called whenever the leading edge of an incoming signal present digital pulse generates an interrupt via the digital input 46 (FIG. 6, Pin 21 of PIC 16F872). The falling insect simultaneously results in a sensor analog voltage signal applied to the analog input 44 of microcontroller 36 whose instantaneous amplitude is determined by the size of the insect, indicative of its species as sensed by the amount of the beam being blocked. This is true because the size of the falling insect is smaller than the diameter of the beam. The interrupt service routine stores the maximum analog value (Target Peak Amplitude) as described above in the detailed description. The stored value is achieved during the excursion of the insect through the beam and is statistically proportional to the size of the insect. However, due to the nonuniform cross-sectional intensity of the infrared beam, the nonuniform cross-sectional sensitivity of the phototransistor 32, and the random orientation and pathway of insects as they pass through the beam, there can be significant variability in the distribution of these Target Peak Amplitudes obtained when multiple insects of the same species fall through the beam. These distributions for different insect species may overlap as described above in the detailed description. In those situations, where the identity of the species cannot be ascertained with absolute certainty, it can be narrowed down to those with similar body size, and then may be narrowed down even further by knowing the predominant species in a particular geographic region. Even if there is still uncertainty, there may still be enough information to make insect control management decisions without visual inspections of the infested commodity since the destructive potential of different species is generally proportional to their body size.

Since the signal present digital pulse is generated whenever any size object passes through the beam, objects smaller or larger than stored-product insects of concern will also get recorded. However, since their Target Peak Amplitudes are recorded, these detections will not erroneously be counted as stored-product weevils or beetles as described above in the detailed description.

The interrupt service routine monitors the duration of the signal present digital pulse as described above in the detailed description. Since the range of time it takes for an object to fall through the infrared beam is known to be greater than about 2 msec and less than about 30 msec, the microcontroller is programmed to not record events when the signal present digital pulse durations are outside of this range in order to prevent false positives (erroneous counts)as described above in the detailed description. For example, in the unlikely event that an insect is able to loiter in the vicinity of the infrared beam, either by dangling above the beam or by crawling onto the surface of the infrared transducers, a series of false signal present digital pulses may be generated. However, these are almost always greater than about 30 msec in duration and would therefore not be recorded. To provide additional protection against false positives due to loitering insects, microcontroller 36 is programmed to not record any signal present digital pulse generated within an about 100 msec retrigger interval of the end of a previously generated signal present digital pulse as described above in the detailed description. This retrigger interval also prevents multiple counts from being recorded when a single insect falls through the beam, either due to an irregular (double peaked) shaped analog waveform or due to grain particles being pulled in by the insect when it enters the probe.

The above features are accomplished by the signal processing sub-component as shown in the software flowchart (FIG. 5) and described above in the detailed description. For the infrared transducers example, the known minimum acceptable period for the signal present digital pulse is about 2 msec, the known maximum acceptable period for the signal present digital pulse is about 30 msec, the retrigger interval is about 100 msec, and the expiration interval of the long-pulse timer is about 250 msec. The about 250 msec long-pulse timer insures that the maximum duration of the interrupt service routine is limited to about 280 msec which occurs in the non-retrigger case when the maximum acceptable period of about 30 msec in the analysis loop is followed by a time-out of the about 250 msec long-pulse timer.

Newly manufactured infrared probes have an initial range of response sensitivity due to component tolerances as described above in the detailed description, and additionally include infrared beam alignment. The first initialization procedure for an infrared probe includes dropping a number of precision steel balls through the exact center of the infrared beam. A Mean of the Ball target Peak Amplitudes (MBPA) for these drops is permanently recorded in the non-volatile memory of the microcontroller chip as a calibration factor. The second initialization procedure of the infrared probe involves the system self-test feature. The microcontroller can generate a digital test pulse (FIG. 6, Pin 24 of PIC16F872) that results in a reduction in the normal current supplied to the infrared LED. This results in a momentary decrease in the amount of infrared light received by the phototransistor, which simulates the passing of an insect through the beam. The second initialization procedure performs a self-test on each newly manufactured probe and the resulting Initial Self-test Peak Amplitude (ISPA) is permanently recorded in the microcontroller's non-volatile memory. This self-test is performed at regular intervals as described above in the detailed description. By performing this self-test at regular intervals during operation, the system can validate proper operation of each probe. The data generated by the self-test as well as the data from the first initialization procedure is all used to make all probes appear to have identical sensitivity response performance as described above in the detailed description of the invention.

The foregoing detailed description is for the purpose of illustration. Such detail is solely for that purpose and those skilled in the art can make variations without departing from the spirit and scope of the invention.

INDEX OF THE ELEMENTS

10. Microcontroller-based insect monitoring system
12. Probe
13. Upper Body Section
16. Aperture
24. Sensor Head
30. Infrared Light-Emitting Diode
31. Beam
32. Phototransistor
33. Temperature Sensor
34. Probe Circuit Board
35. Beam Current Generator
36. Programmable Microcontroller
37. Internal Non-Volatile Memory
38. Current to Voltage Convertor
39. Capacitive Coupling
40. Voltage Threshold Detector
41. Bias Reference Voltage
42. Central Location Device
44. Analog Input
46. Digital Input
48. Digital Output
50. Multiplexer
52. Transmission Medium

What is claimed is:

1. A method for detecting insect infestation in stored products comprising:
    (a) placing a grain probe detector containing (1) a sensor head having at least one transducer for detecting the passage of at least one insect through the probe sensor head, and (2) a circuit board operatively connected to said transducers; into a stored product,
    (b) detecting the passage of at least one insect through the probe and providing an analog output, and generating a signal present digital pulse in said circuit board based on said analog output,
    (c) determining if said signal is greater than threshold level,
    (d) sending said signal greater than threshold level to a microcontroller on said circuit board,
    (e) processing said signal to extract data from said signal, and
    (f) storing said signal process in a memory of said microcontroller.

2. The method of claim 1 further comprising:
    sending said data stored by said memory to a central location device for analysis.

3. A computer readable medium encoded with a software program for monitoring insects in stored products wherein said program (a) analyzes an incoming analog sensor signal when an incoming signal present digital pulse is detected, (b) measures duration of the signal present digital pulse, (c) monitors the analog sensor signal for a maximum analog value, (d) records and stores a maximum analog value to form a target peak amplitude for transmission to a central location device, and (e) records and stores time of occurrence of said maximum analog value.

4. The computer readable medium of claim 3 wherein said program further calibrates new grain probe detectors for consistent performance by (a) determining a standard mean target peak amplitude creating a first calibration factor, and (b) recording and storing said standard mean target peak amplitude for transmission to said central location device.

5. The computer readable medium of claim 4 where said program further self-tests new grain probe detectors to validate the operation of at least one grain probe detector by (a) generating a digital test pulse to simulate an insect passing said transducer to obtain an initial self-test peak amplitude creating a second calibration factor, (b) recording and storing said initial self-test peak amplitude for transmission to a central location device.

6. The computer readable medium of claim 5 wherein said program self-tests grain probe detectors that are in operation in a stored product by:

(a) generating a digital test pulse to simulate an insect passing said transducer to obtain a current self-test peak amplitude creating a third calibration factor, (b) recording and storing said current self-test peak amplitude for transmission to a central location device.

7. A method for detecting insect infestation in stored products comprising:

(a) placing a grain probe detector containing (1) a sensor head having at least one transducer for detecting passage of at least one insect through the probe sensor head, and (2) a circuit board operatively connected to said transducers; into a stored product, (b) detecting the passage of at least one insect through the probe and providing an analog output, and generating a signal present digital pulse in said circuit board based on said analog output, (c) determining if said signal is greater than threshold level, (d) sending said signal greater than threshold level to a microcontroller on said circuit board, (e) processing said signal to extract data from said signal, using a computer readable medium having a software program which (1) analyzes said analog sensor signal when an incoming signal present digital pulse is detected, (2) measures duration of the signal present digital pulse, (3) monitors the analog sensor signal for a maximum analog value, (4) records and stores a maximum analog value to form a target peak amplitude for transmission to a central location device, and (5) records and stores time of occurrence of said maximum analog value.

8. The method of claim 7 further comprising:

sending said stored data to a central location device for analysis.

9. The method of claim 8 further comprising self-testing said grain probe detectors wherein said program (1) generates a digital test pulse to simulate an insect passing said transducers to obtain a current self-test peak amplitude creating a calibration factor, (2) recording and storing said current self-test peak amplitude for transmission to a central location device.

10. A system for quantitative and/or qualitative detection of insect infestation in stored products comprising:

(a) at least one grain probe detector containing;

(1) a sensor head having at least one transducer for detecting the passage of at least one insect through said probe head and producing an analog output wherein said output is a waveform, and (2) a circuit board operatively connected to said transducers for collecting and storing data generated by said transducers wherein said circuit board comprises a programmable microcontroller and a voltage threshold detector, and (b) a central location device operatively connected to said circuit board for collecting circuit board data for further processing and storage.

11. The system of claim 10 wherein said microcontroller includes an analog input, a digital input, and an internal non-volatile memory.

12. The system of claim 10 wherein said microcontroller contains a computer readable medium having:

(a) a signal processing sub-component which analyzes an incoming sensor signal to determine if the signal is produced by an insect falling through the sensor head by checking a signal present digital pulse duration; when said signal is produced by a falling insect, said sub-component determines a maximum analog value during a pulse interval, said sub-component time stamps said determined maximum analog value and stores the maximum analog value and the time stamp;

(b) a calibration sub-component; and (c) a data transmission sub-component.

13. The system of claim 12 wherein said calibration sub-component comprises at least two response sensitivity initialization routines in order to obtain calibration factors.

14. The system of claim 10 wherein said probe includes a temperature sensor operatively connected to said circuit board.

* * * * *